United States Patent [19]

Tahara et al.

[11] Patent Number: 4,857,529
[45] Date of Patent: Aug. 15, 1989

[54] INTERFERON INDUCING, ANTI-VACCINIA, AND/OR ANTI-INFLUENZA COMPOSITIONS

[75] Inventors: Yoshiyuki Tahara, Ohi; Hiroyasu Koyama, Ageo; Yasuhiro Komatsu, Niiza; Reiko Kubota, Tokyo; Toshihiro Takahashi, Ohi, all of Japan

[73] Assignee: Nisshin Flour Milling Co., Ltd., Japan

[21] Appl. No.: 178,510

[22] Filed: Apr. 7, 1988

Related U.S. Application Data

[62] Division of Ser. No. 256,579, Apr. 22, 1981, Pat. No. 4,755,601.

[30] Foreign Application Priority Data

Apr. 23, 1980 [JP] Japan .................... 55-55108

[51] Int. Cl.$^4$ ................ A61K 31/495; A61K 31/445; A61K 31/40; A61K 31/415
[52] U.S. Cl. .................... 514/255; 514/315; 514/385; 514/408; 514/428
[58] Field of Search ............ 514/255, 315, 385, 408, 514/428

[56] References Cited

U.S. PATENT DOCUMENTS 4,265,910 5/1981 Tahara et al. .................... 514/671
4,271,810 9/1980 Tahara et al. .................... 514/671
4,324,910 4/1981 Tahara et al. .................... 564/462
4,755,601 7/1988 Tahara et al. .................... 544/410

FOREIGN PATENT DOCUMENTS 2079395 12/1981 United Kingdom .

OTHER PUBLICATIONS

Tahara et al., "Anti-Ulcer Polyprenyl Alcohols", Chem. Abst. 92:129133z, (1979).
Tahara et al., "Pharmaceuticals for Immune Enhancement," Chem. Abst. 93:173714j.
Tahara et al., Chem. Abst. 95-203998r.
Tahara et al., Chem. Abst. 96-143116k.
Tahara et al., Chem. Abst. 98-215840h, 215841j.

Primary Examiner—Cecilia Shen
Attorney, Agent, or Firm—Jordan B. Bierman

[57] ABSTRACT

New antiviral nonaprenylamine derivatives represented by the following formula

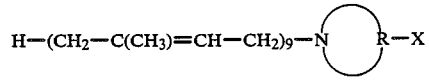

wherein R is 4 or 5 atoms selected from the group consisting of C and N so as to complete, with the non-R nitrogen, a 5- or 6-membered heterocyclic ring, and X is selected from the group consisting of H and hydroxy-lower alkyl and non-toxic, pharmaceutically acceptable acid addition salts thereof and a pharmaceutically acceptable carrier.

4 Claims, No Drawings

INTERFERON INDUCING, ANTI-VACCINIA, AND/OR ANTI-INFLUENZA COMPOSITIONS

PRIOR APPLICATION

This application is a division of copending U.S. patent application Ser. No. 256,579 filed Apr. 22, 1981, now U.S. Pat. No. 4,755,601.

This invention relates to new nonaprenylamine derivatives and the acid addition salts thereof, which are useful for controlling virus infection of vertebrate animals.

There are known heretofore various substances, which have been decided to have preventive or alleviative effects on diseases caused by virus whose host is a vertebrate animal, or which have been recognized to be capable of alleviating symptoms of the diseases by significantly enhancing antibody activity in the animal. Antivirotics reported so far include interferon, substances capable of inducing interferon, i.e. inducers (interferon inducers, amantadine hydrochloride or synthetic substances, such as methysazone, which directly exert inhibitory effect on the virus propagation. Interferon is glycoprotein having antiviral and antitumor activity, said glycoprotein being produced in situ by cells of a vertebrate animal when the cells are infected with virus, and is effective against very wide range of virus-infected diseases. Known inducers, which induce interferon in vertebrate animals by a process other than the virus infection, include natural high molecular substances such as double chain ribonucleic acid of bacteriophage of a certain species, or synthetic high molecular substances such as double chain ribonucleic acid, typical of which is polyinosinic acid-polycytidylic acid, or low molecular inducers such as tyrolone.

In the production of interferon, however, there is involved a problem how to carry out the purification thereof, and in fact no economical proces for the production thereof has not been established yet. On the other hand, conventional interferon inducers have not been put to practical use mainly because of toxicity thereof. Synthetic antiviral agents which directly exert inhibitory effect on the virus propagation, which are commercially available at present, have a rather narrow range of virusinfected diseases which are curable by administration of said agent, and thus the advent of novel synthetic antiviral agents is earnestly desired. Taking such circumstances into consideration, the present inventors extensively conducted studies in finding compounds capable of producing interferon of high potency and, moreover, having antiviral activity on the biological level, and as the result they have eventually found new nonaprenylamine derivatives of the following general formula (I) and acid addition salts thereof, which show excellent interferon inducing ability and, at the same time, demonstrate excellent antiviral and antitumor activity even in the biological test, and which are thus expected as a medicament.

New nonaprenylamine derivatives of this invention are represented by the following general formula

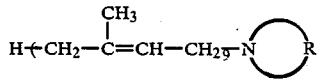

wherein R is an atomic grouping capable of forming together with the adjcent nitrogen atom a 5- or 6-membered heterocyclic ring, which may contain an additional hetero atom, said R optionally being substituted with a hydrogen atom or a hydroxy lower alkyl group, provided that said additional hetero atom is a nitrogen atom.

For the production of nonaprenylamine derivative of this invention represented by the above-mentioned general formula (I) and acid addition salts thereof, there may be adopted a process in which the known procedures for the amine synthesis are applied to the starting nonaprenol (solanesol) represented by the formula

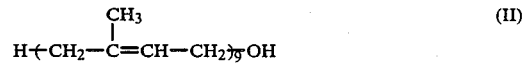

to produce a corresponding amine derivative.

Further, the amine derivative thus obtained may be converted into a corresponding salt in the usual way. More specifically, a desired amine can be produced according to a process which comprises converting nonaprenol of the aforesaid general formula (II) into a corresponding halide (e.g. solanesyl bromide) or aryl sulfonic acid ester (e.g. solanesyltosylate), followed by reaction with a heterocyclic derivative having at least one secondary amino group in the presence or absence of a base to produce the desired amine derivatives. An acid addition salt of the amine derivative thus obtained can be obtained by mixing said amine in an appropriate solvent with a desired acid to form a salt and crystallizing the salt out of the solution by evaporation or other means to recover the same. The acid addition salts suitable for use as medicines include, for example, those with hydrochloric acid, acetic acid, citric acid, fumaric acid, lactic acid and the like.

The compounds represented by the general formula (I) and acid addition salts thereof are illustrated below with reference to preparative example.

PREPARATIVE EXAMPLE 1

N-solnesylpiperadine diydrochloride

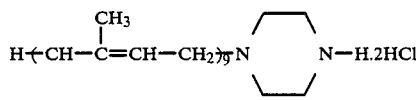

To a mixture of piperadine (9.3 g.), ethanol (50 ml) and isopropylether (30 ml) a solution of solanesyl bromide (10 g.) in isopropylether (20 ml) was added dropwise at room temperature for 2.5 hours with stirring, which was continued for further 1 hour, followed by standing overnight. To the resulting reaction mixture a solution of sodium hydroxide (4 g.) in water (20 ml) was dropwise added with ice-cooling and stirring and then extracted with isopropylether. The extract was washed successively with water and saturated saline, dried over with anhydrous sodium sulfate and then concentrated under reduced pressure. The residue (9.4 g.) was purified by column chromatography using silica gel (100 g.). Elution was carried out with chloloform-methanol. The initially eluted fraction (7.3 g.) was dissolved in ethyl acetate (200 ml), added with an ether solution containing 6N HCl to weakly acidic and then cooled. The crystallized mass was separated by filtration to recover N-solanesylpiperadine dihydrochloride (5.1 g.), m.p.

137°–140° C. Elementary analysis as $C_{49}H_{82}N_2 \cdot 2HCl \cdot 3/2H_2O$ showed the following:

|  | C % | H % | N % |
|---|---|---|---|
| Calcd. | 73.64 | 10.97 | 3.51 |
| Found | 73.83 | 10.91 | 3.48 |

PREPARATIVE EXAMPLES 2 TO 7

The same procedures as in Example 1 were carried out for the reaction of solanesyl bromide with a heterocyclic derivative having secondary amino group thereby to produce the below-indicated compounds, the structural formula, molecular formula, melting point and elementary analysis of which also are listed in Table 1.

thereon and thereby to calculate the plaque inhibition rate in each of the test groups against a group to which no test compound had been administered. The plaque inhibition rate of each test compound is shown in Table 2.

(2) Effect on mice infected with vaccinia virus

Groups, each consisting of 10 ICR female mice weighting about 15 g., were intravenously injected with 0.1 ml of a vaccinia virus (DIE strain) dilution through the vein of tail at the distance of 2 cm from the room of the tail. On the 8th day after the inoculation, the number of lesions in form of small pocks on the tail surface was counted after dyeing the tail with a solution containing 1% fluorescein and 0.5% methylene blue. In this test, each test compound was administered intraperitoneally to the mice on the day just before inoculation of the virus, whereby antivirus activity of the test compound

TABLE 1

| Prep. Examp. No. | Structure | Molecular formula | m.p. (°C.) | Elementary analysis Calculated (%) C / H / N | Found (%) C / H / N |
|---|---|---|---|---|---|
| 2 | H$+$CH$_2$—C(CH$_3$)=CH—CH$_2$$)_9$N⟨cyclohexyl⟩ | $C_{50}H_{83}N \cdot HCl \cdot H_2O$ | 105–107 | 79.78  11.52  1.86 | 79.64  11.42  1.82 |
| 3 | H$+$CH$_2$—C(CH$_3$)=CH—CH$_2$$)_9$N⟨morpholino⟩O | $C_{49}H_{81}ON \cdot HCl \cdot H_2O$ | 108–111 | 77.99  11.22  1.86 | 77.92  11.02  1.80 |
| 4 | H$+$CH$_2$—C(CH$_3$)=CH—CH$_2$$)_9$N⟨thiomorpholino⟩S | $C_{48}H_{79}NS \cdot HCl$ | 104–107 | 78.05  10.92  1.90 | 78.08  10.91  1.98 |
| 5 | H$+$CH$_2$—C(CH$_3$)=CH—CH$_2$$)_9$N⟨pyridyl⟩ | $C_{48}H_{76}N_2$ | 62–64 | 84.64  11.25  4.11 | 84.47  11.19  4.10 |
| 6 | H$+$CH$_2$—C(CH$_3$)=CH—CH$_2$$)_9$N⟨piperazinyl-CH$_2$CH$_2$OH⟩ | $C_{51}H_{86}ON_2$ | 41–42 | 82.41  11.66  3.77 | 81.98  11.57  3.70 |

Physiological effects of the compounds of the present invention are illustrated below in detail.

(1) Interferon inducing activity test

Each test compound suspended in water with a surfactant was intraperitoneally administered to each group consisting of 5 ICR female mice weighing about 25 g. Twenty hours after administration, blood was collected from the mice and serum was separated therefrom to obtain a serum interferon. The following steps were taken in order to determine potency of the serum interferon thus induced. L-929 cells derived from mice and incubated previously in a monolayer was brought into contact with the test serum solution diluted 10 times, incubated overnight at 37° C. in an incubator placed in carbon dioxide atmosphere and the dilute test serum solution was removed therefrom. Thereafter, the cells were inoculated with vesicular stomatitis virus and placed on a tissue culture medium containing 1% agar. After incubation at 37° C. for 24 hours, the cells were dyed with neutral red solution diluted to an appropriate concentration to count the number of plaques formed was evaluated in terms of inhibition of tail lesions as calculated in each test group against a group to which no test compound had been administered.

The rate of tail lesion inhibition of each test compound is shown in Table 2.

(3) Effect on mice infected with influenze virus

Groups, each consisting of 10 ICR female mice weighing about 25 g. were challenged by intralation of neblyzed influenza virus A/PR-8. A solution of each test compound in an aqueous solution containing a surfactant was intraperitoneally administered to the mice 24 hours and 3 hours before the virus infection, and 5 times every other day from the second day after the infection. The mice that survived 21 days after the challenge were regarded as survivors, and survival rate was obtained according to the following equation.

$$\frac{\text{Number of survivors}}{\text{Number of mice treated}} \times 100 = \text{survival rate (\%)}$$

TABLE 2

| Test compound | Dose (i.p.) mg/kg | Prevention from vaccinia infection (Inhibition of tail lesion) % | Serum interferon (Plaque inhibition %) | Dose (i.p.) mg/kg | Prevention from influenza infection (Survival rate) % |
|---|---|---|---|---|---|
| N—β-hydroxyethyl-N'-solanesylpiperazine | 50 | 88.7 | 58.1 | 30 | 40 |
| Amantadine hydrochloride (Control) | 50 | — | — | 30 | 30 |

(4) Toxicity

In order to investigate acute toxicity of the compounds of the present invention, 50% lethal dose of each compound was obtained by using ddY male mice weighing 20–25 g. From the results shown in Table 3, it is understood that the compounds had high safety margin by intraperitoneal administration.

TABLE 3

| | 50% Lethal dose (mg/kg) | |
|---|---|---|
| Test compound | Intravenously administered | Intraperitoneally administered |
| N—β-hydroxyethyl-N'—solanesylpiperazine | 150 | >500 |

As is clear from the foregoing test results, the active ingredients of the present invention have interferon inducing activity in vivo and are low in toxicity with showing excellent antiviral activity. In the light of the fact that the strict correlation of interferon activity with the individual antiviral activities is not always observed for the present ingredients, there is considered also a possibility that the antivirus activities of said ingredients at biological level are concerned not only in interferon but also in other defensive mechanism of host. There are known various human diseases caused by virus, such as herpes-infected diseases (e.g. herpes simplex), influenza, measles and the like. Accordingly, when the active ingredients of the present invention are used for prevention and treatment of virus-infected diseases, they are administered to patients by such techniques involving oral, inhalant, or the like administration as well as subcutaneous, intramascular and intravenous injection. According to the condition of patient such as age, symptom and route by which the ingredient is administered, the active ingredient of the present invention is used in a dose of 0.5–20 mg/kg, preferably 3–5 mg/kg several times (2–4 times) per day.

The active ingredients of the present invention can be formulated into compositions for medication, for example, tablets, capsules, granules, powder, liquid preparation for oral use, eye lotions, suppositories, ointments, injections and the like, according to any conventional method.

When the present active ingredients are orally administered, they may be formulated into tablets, capsules, granules or powder. These solid preparations for oral use may contain commonly used excipients, for example, silicic anhydride, metasilicic acid, magnesium alginate, synthetic aluminum silicate, lactose, cane sugar, corn starch, microcrystalline cellulose, hydroxypropylated starch or glycine, and the like; binders, for example, gum arabic, gelatin, tragacanth, hydroxypropyl cellulose or polyvinylpyrrolidone; lubricants, for example, magnesium stearate, talc or silica; disintegrating agents, for example, potato starch and calcium carboxymethyl cellulose; or wetting agents, for example, polyethylene glycol, sorbitan monooleate, polyoxyethylene-hardened castor oil, sodium laurylsulfate. In preparing soft capsules, in particular, the present active ingredients may be formulated by dissolving or suspending them in polyethylene glycol or commonly used oily substrates such as sesame oil, peanut oil, germ oil, fractionated coconut oil such as Miglyol ®, or the like. Tablet or granule preparations may be coated according to the usual method.

Liquid preparation for oral use may be in the form of aqueous or oily emulsion or syrup, or alternatively in the form of dry product which can be re-dissolved before use by means of a suitable vehicle. To these liquid preparations, there may be added commonly used additives, for example, emulsifying aids such as sorbitol syrup, methyl cellulose, gelatin, hydroxyethyl cellulose and the like; or emulsifiers, for example, lecithin, sorbitan monooleate, polyoxyethylene-hardened castor oil, non-aqueous vehicles, for example, fractionated coconut oil, almond oil, peanut oil and the like; or antiseptics, for example methyl p-hydroxybenzoate, propyl p-hydroxybenzoate or sorbic acid. Further, these preparations for oral use may contain, if necessary, preservatives, stabilizers and the like additives.

In case where the present active ingredients are administered in the form of non-oral suppository, they may be formulated according to the ordinary method using oleophilic substrates such as cacao oil or Witepsol ®, or may be used in the form of rectum capsule obtained by wrapping a mixture of polyethylene glycol, sesame oil, peanut oil, germ oil, fractionated coconut oil and the like in a gelatin sheet. The rectum capsule may be coated, if necessary, with waxy materials.

When the present active ingredients are used in the form of injection, they may be formulated into preparations of oil solution, emulsified solution or aqueous solution, and these solutions may contain commonly used emulsifiers, stabilizers or the like additives.

According to the method of administration, the above-mentioned compositions can contain the present active ingredients in an amount of at least 1%, preferably 5 to 50%.

The procedure of formulating the present active ingredients into various preparations is illustrated below with reference to Pharmaceutical Examples.

PHARMACEUTICAL EXAMPLE 1

Hard capsule preparations for oral use

A mixture of 25 g. of N-β-hydroxyethyl-N'-solanesylpiperazine and 7.5 g. of polyoxyethylene castor oil in acetone was mixed with 25 g. of silicic anhydride. After evaporation of the acetone, the mixture was mixed further with 5 g. of calcium carboxymethylcellulose, 5 g. of corn starch, 7.5 g. of hydroxypropylcellulose and 20 g. of microcrystalline cellulose, and 30 ml of water was added thereto and kneaded to give a granular mass. The mass was pelletized by means of a pelletizer (ECK pelletter of Fuji Paudal Co., Japan) equipped with No. 24 mesh (B.S.) screen to obtain granules. The granules were dried to less than 5% moisture content and screened with No. 16 mesh (B.S.) screen. The screened granules were capsuled by means of a capsule filling machine so as to be contained in an amount of 190 mg per capsule.

PHARMACEUTICAL EXAMPLE 2

Soft capsule preparations for oral use

A homogeneous solution was prepared by mixing 50 g. of N-solanesylpiperazine dihydrochloride with 130 g. of polyethylene glycol (Macrogol 400). Separately, a gelatin solution was prepared which contained 93 g. of gelatin, 19 g. of glycerine, 10 g. of D-sorbitol, 0.4 g. of ethyl p-hydroxybenzoate, 0.2 g. of propyl p-hydroxybenzoate and 0.4 g. of titanium oxide and which was used as a capsule film forming agent. The previously obtained solution, together with the capsule film forming agent, was treated with a manual type flat punching machine to obtain soft capsules each having the contents of 180 mg.

PHARMACEUTICAL EXAMPLE 3

Injections

A mixture of 5 g. of N-β-hydroxyethyl-N'-solanesylpiperazine, an appropriate amount of peanut oil and 1 g. of benzyl alcohol was made a total volume of 100 cc by addition of peanut oil. The solution was portionwise poured in an amount of 1 cc under asepsis operation into an ampule which was then sealed.

PHARMACEUTICAL EXAMPLE 4

Injections

A mixture of 1.0 g. of N-solanesylpiperazine dihydrochloride, 5.0 g. of Nikkol HCO-60 (a tradename) (hydrogenated castor oil polyoxyethylene-60 mols-ether), 20 g. of propylene glycol, 10 g. of glycerol and 5.0 g. of ethyl alcohol was mixed with 100 ml of distilled water and stirred. Under asepsis operation, the solution was portionwise poured in an amount of 1.4 ml into an ampule which was then sealed.

What we claim is:

1. A pharmaceutical composition comprising an interferon inducing, anti-vaccinia, and/or anti-influenza effective amount of a compound of the formula

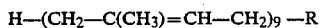

$$H-(CH_2-C(CH_3)=CH-CH_2)_9-R \qquad I$$

wherein R is a heterocyclic group selected from

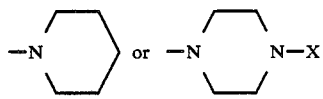

and X is selected from the group consisting of H and hydroxy-lower alkyl and non-toxic, pharmaceutically acceptable acid addition salts thereof and a pharmaceutically acceptable carrier.

2. The composition of claim 1 wherein the compound is N-solanesylpiperidine.

3. The composition of claim 1 wherein the compound is N-(β-hydroxyethyl)-N'-solanesylpiperazine.

4. The composition of claim 1 wherein the compound is N-solanesylpiperazine dihydrochloride.

* * * * *